United States Patent
Zhu

(10) Patent No.: US 6,171,810 B1
(45) Date of Patent: *Jan. 9, 2001

(54) METHOD FOR DETECTING AND ASSAYING EXOGLYCOSIDASE ACTIVITY

(75) Inventor: Alex Zhu, New York, NY (US)

(73) Assignee: New York Blood Center, Inc., New York, NY (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/287,869

(22) Filed: Apr. 7, 1999

(51) Int. Cl.[7] .................. C12Q 1/34; C12Q 1/54; C12Q 1/00

(52) U.S. Cl. ........................ 435/18; 435/14; 435/4; 435/968; 536/1.11; 536/123.13; 536/123.1

(58) Field of Search .................. 435/18, 14, 4, 435/968; 536/1.11, 123.13, 123.1

(56) References Cited

U.S. PATENT DOCUMENTS 3,850,322 * 4/1976 Thomas et al. ............... 435/18

OTHER PUBLICATIONS

Robinson et al, Clinica Chimica Acta, vol. 55, p65–69, 1974.*

McGuire et al., Methods in Enzymology, vol. XXVII:755–763 (1972).

Coughlan, et al., Biotechnol. Appl. Biochem., 17:259–289 (1993).

Hendrikx, et al., Analytical Biochemistry, 222:456–460 (1994).

Tyagarajan, et al., Glycobiology, vol. 6, No. 1:83–93 (1996).

Withers, et al., Protein Science, 4:361–372 (1995).

Biochemical Journal, 311:349–351 (1995).

Zhang, et al., Proc. Natl. Acad. Sci. USA, vol. 94:4504–4509 (Apr. 1997).

* cited by examiner

Primary Examiner—Louise N. Leary
(74) Attorney, Agent, or Firm—Amster, Rothstein & Ebenstein

(57) ABSTRACT

A method for detecting and measuring exoglycosidase activity is presented. The method employs derivatives containing the fluorescent group 4-methylumbelliferyl ("4-Mu") at a pH lower than that conventionally employed. While the fluorescence intensity due to the 4-Mu group is considerably diminished at the lower pHs employed, the fluorescence intensity is still sufficient to continuously measure exoglycosidase activity in the activity range commonly assayed. The method is easily adaptable to high throughput enzyme assay systems and automated data analysis method. The method also provides a means to detect alterations in exoglycosidase activity that are independent of expression levels.

17 Claims, 1 Drawing Sheet

METHOD FOR DETECTING AND ASSAYING EXOGLYCOSIDASE ACTIVITY

FIELD OF THE INVENTION

Glycosidases, enzymes which hydrolyze glycosidic bonds, are a diverse group of enzymes widely present in nature. Glycosidases are important in a number of biological processes, and a number of disease states have been linked to defects in these enzymes. For example, an absence of lysosomal α-glucosidase leads to a fatal condition, Pompe disease, and defects in glucocerebrosidase activity lead to Gaucher's disease. In addition, elevated serum levels of some glycosidases are correlated with the presence of cancerous cells. Glycosidases are also important in industrial processes ranging from food processing (fruit juice processing, lactose reduction, production of "invert" sugar) to textile processing, pulp processing in papermaking, and biomass degradation.

Exoglycosidases are a subset of glycosidases that hydrolyze a terminal sugar residue from polysaccharides and/or glyconconjugates. Examples of exoglycosidase include fucosidases, glucosidases, galactosidases, and mannosidases. Due to their involvement in a variety of biological phenomena and potential application in biotechnological and industrial settings, there has been a great deal of interest in understanding the active sites and catalytic mechanisms of these enzymes. In addition, through the use of various mutagenesis strategies, efforts have been made to alter and improve the properties of wild-type exoglycosidases, including their specific activities, thermostabilities, substrate specificities and pH optima.

A powerful mutagenesis strategy for the study of enzymes, including exoglycosidases, is directed evolution. In this technique, clones expressing the gene for the enzyme of interest are subjected to multiple rounds of mutagenesis, functional screening, and amplification. More particularly, cells bearing the gene of interest are first subjected to mutagenesis, then a selected number of clones are individually screened for a desired change in activity. The most desirable clones are retained, and the DNA bearing the gene of interest is then pooled from these clones and used to transform cells for the next round of mutagenesis. In this manner, the desired phenotype, as dictated by the functional screening, is enhanced with each round. Using directed evolution, β-fucosidase activity was obtained from a β-galactosidase gene after seven rounds of mutagenesis, screening, and amplification (Zhang et al., *Proc Natl Acad Sci U S A* 94(9):4504–4509 (1997)).

However, such directed evolution methods are generally labor-intensive and time-consuming. For example, in the work described above, 10,000 clones were visually screened in each round. The labor-intensive nature of this method limits the number of initial clones, the number of rounds of mutagenesis and screening, and the number of enzyme activities that can be tested in any series of experiments. In addition, in performing directed evolution, it is crucial to distinguish between those clones which express mutated enzymes, and those clones whose change in enzyme activity are due to alterations in the level of expression of the enzyme gene. This determination requires an additional step to measure the amount of enzyme inside the cell. This additional step increases the time, cost and labor required for the entire process.

Separate measurements of the amount of enzyme in the cell can be avoided by taking advantage of enzyme kinetic parameters that are independent of the amount of enzyme in a cell sample. By screening for changes in these parameters, alterations in the structure of the enzyme, rather than in its expression level, can be easily detected. However, these measurements often require many additional experiments to determine the true enzyme activity. Thus, although they avoid the need to measure the level of enzyme in the cells, these additional experiments also increase the time, cost and labor required for the entire process.

Directed evolution methods are generally paired with high throughput enzyme assay systems to minimize the time, cost and labor required in assaying a large number of samples. High throughput enzyme assay systems utilize robots and automatic data analysis methods to simultaneously analyze many samples with minimal operator interaction. These systems may also utilize other common laboratory supplies, such as 96-well or 384-well microplates and disposable pipet tips, to further lower costs and time associated with assay of the samples. By using a high throughput enzyme assay system, many experiments can be simultaneously performed at a low cost.

4-methylumbelliferyl (hereinafter "4-Mu")-linked monosaccharide derivatives are commonly used substrates for assays of exoglycosidase activity. The fluorescence intensity of 4-Mu is pH-dependent, and is maximal above a pH of 9. However, a majority of exoglycosidases are most active below neutral pH, that is, below a pH of about 7.0. In conventional in vitro endpoint assays of exogylcosidase activity that employ such a 4-Mu-linked substrate, the enzyme and the substrate are incubated at the pH that is optimal for the activity of the enzyme for a defined period of time. The enzyme cleaves the 4-Mu moiety from the substrate. Thereafter, the reaction is terminated by addition of a high-pH buffer (pH between 9.5 and 10.5). This buffer both terminates the reaction and enhances the fluorescence intensity of the 4-Mu product, thereby increasing the sensitivity of the assay. The amount of the liberated 4-Mu moiety generated is measured by fluorescence spectroscopy, usually using an excitation wavelength around 365 nm and emission wavelength around 440 nm. By varying the amount of substrate or the assay environment, values for various enzyme kinetic parameters can be determined.

In high throughput enzyme assay systems, it is conventional to employ endpoint assays. In endpoint assays, the reaction between the enzyme and its substrate is halted before the amount of product is measured. However, in determining enzyme kinetic parameters, endpoint assays are not desirable, because a separate experiment is required to generate data for each time point, and many such experiments must be run to generate sufficient data to determine the enzyme kinetic parameter values in each sample. In such experiments, kinetic assays are more appropriate than endpoint assays. In a kinetic assay, the amount of the product generated by the reaction of the enzyme with the substrate is measured at various time points while the reaction is in progress. Kinetic assays speed up the measurement of enzyme kinetic parameters by reducing the number of experiments required to obtain the necessary data.

The detection of mutant exoglycosidase enzymes could be accelerated by the use of kinetic enzyme assays in a high throughput enzyme assay system. However, since most exoglycosidases require a much lower pH for optimal activity than that required for maximal fluorescence of the 4-Mu product, kinetic assays have not previously been employed. To date, most exoglycosidase assays have employed either an endpoint assay or have used other compounds to detect activity, e.g., paranitrophenol. Therefore, the lack of a useful kinetic assay for exoglycosidase activity which employs fluorogenic substrates has hampered the application of high throughput enzyme assay systems to the study of these enzymes.

A previous attempt to employ 4-Mu-linked monosaccharide derivatives in a kinetic exoglycosidase assay focused on balancing the pH optima of the enzyme and the product (Hendrikx, P.-J. et al., *Anal. Biochem.* 222:456–460 (1996)). However, this approach is still unsatisfactory for high throughput screening systems, because the deviation from the optimal pH of the enzyme introduces an additional factor into the measurement of potential mutant enzyme activity. Correction for this deviation may slow down the high throughput screening rate.

It is therefore desirable to have an enzyme activity assay system that is adaptable to high throughput screening of exoglycosidases, so as to be able to screen a large number of individual exoglycosidase samples in a short period of time. It would be further desirable to have an enzyme activity assay system that can detect altered exoglycosidase activity and at the same time determine whether that altered activity is due to an alteration in the characteristics of the enzyme, or is merely due to a change in the expression level of the structural gene for the enzyme. Finally, it would be desirable to have an enzyme activity assay system that can simultaneously test multiple substrates and/or inhibitors of a target exoglycosidase activity or activities in a large number of clones.

SUMMARY OF THE INVENTION

The present invention provides a method for assaying exoglycosidase activity using 4-Mu-linked substrates, that, unlike prior art methods, can be used to collect multiple data points from a single sample over a period of time. As a result, the method of the present invention is easily adaptable to high throughput screening methods and automated data analysis techniques. Furthermore, unlike prior art methods, the method is performed at the optimal pH for activity of the enzyme, so corrections for deviation from the optimal pH to arrive at the correct values for specific activity for the enzyme are not required. As used herein, "specific activity" of an enzyme refers to the amount of product produced by the action of the enzyme on a substrate per unit of time and unit of enzyme. The method comprises the steps of contacting a solution containing an enzyme with a substrate having a 4-Mu group at a pH optimal for the specific activity of the enzyme under conditions allowing cleavage of the 4-Mu group from the substrate by the enzyme, and determining the presence and/or the amount of the cleaved 4-Mu group in the solution without the need for adjusting the pH of the solution.

The method of the present invention may be used for detecting and/or measuring exoglycosidase activity in a large number of samples in a short period of time. The method of the present invention can also be used to directly measure enzyme kinetic parameters to detect alterations in enzyme activity that are not due to changes in expression of the genes encoding the enzyme. The method of the present invention may be easily adapted to high throughput enzyme assay systems and automated data analysis methods, and may also be used to distinguish between changes in enzyme specific activity and changes in the levels of expression of the gene encoding that enzyme. The method of the present invention is also useful for simultaneously studying exoglycosidase activity toward different substrates and inhibitors, as well as other changes in the enzyme environment where desired, such as temperature, pH, salt concentration, and other conditions of interest known to those in the art. The method is not limited to the assay of exoglycosidases, but can also be used to assay any other enzyme that can cleave a 4-Mu group from a substrate bearing a cleavable 4-Mu group.

DETAILED DESCRIPTION OF THE INVENTION

Figure 1:
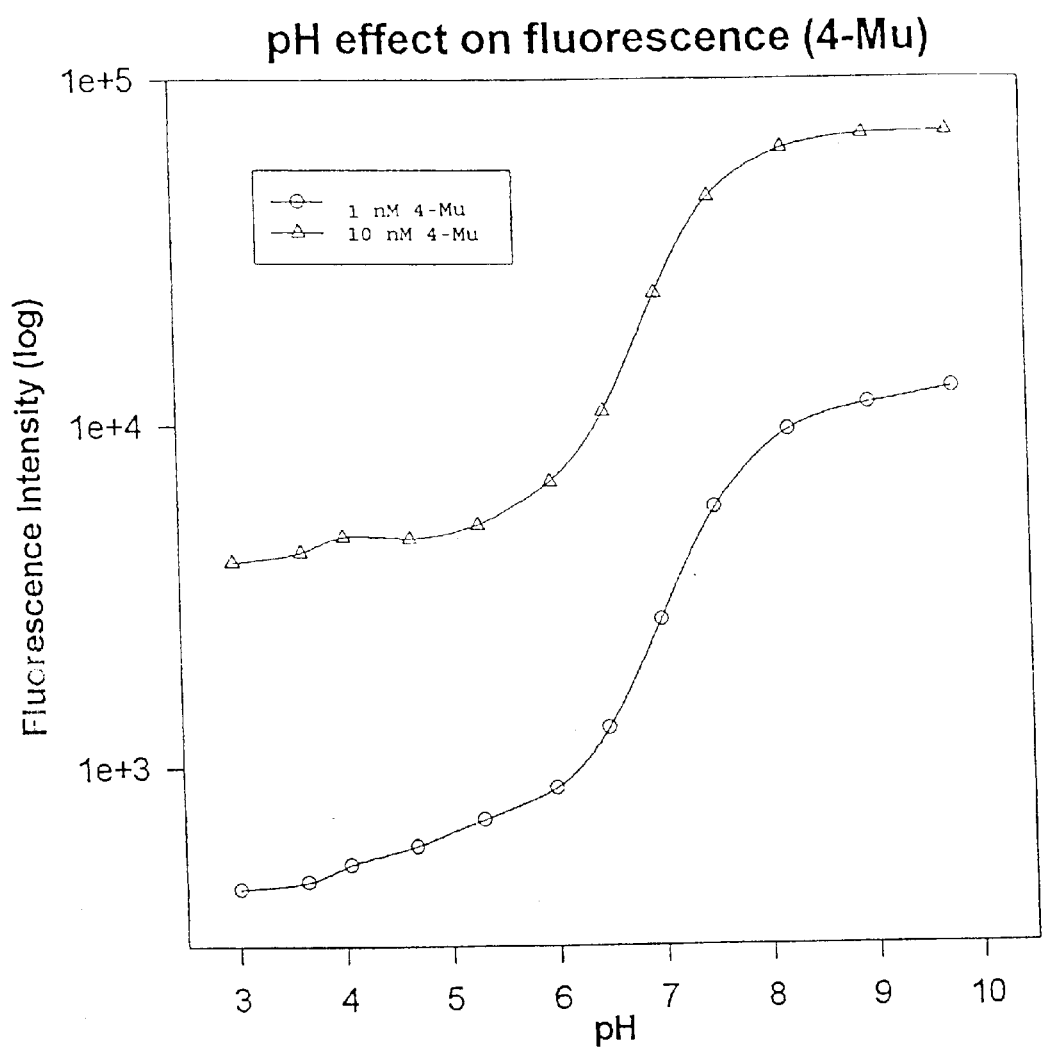
FIG. 1 shows the pH dependence of 4-Mu fluorescence intensity over a pH range between 3 and 10, when measured with an excitation wavelength of 365 nm and an emission wavelength of 440 nm, and at concentrations of 1 and 10 nM, wherein (602) corresponds to 1 nM 4-Mu, and (Δ) corresponds to 10 nM 4-Mu.

The present invention relates to a method for detecting the presence of an enzyme in a solution, comprising the steps of contacting the solution with a substrate having a 4-Mu group at a pH optimal for the specific activity of the enzyme under conditions allowing cleavage of the 4-Mu group from the substrate by the enzyme, and determining the presence of the cleaved 4-Mu group in the solution without adjusting the pH of the solution. The present invention also relates to a method for measuring a kinetic parameter of an enzyme in a solution, comprising the steps of contacting the solution with a substrate having a 4-Mu group with the enzyme at a pH optimal for the specific activity of the enzyme under conditions allowing cleavage of the 4-Mu group from the substrate by the enzyme, and determining a value for the kinetic parameter of the enzyme from the amount of the cleaved 4-methylumbelliferyl group generated in the solution without adjusting the pH of the solution. The enzyme is preferably an exoglycosidase, an endoglycosidase or a heteropolysaccharide side chain-cleaving enzyme, and more preferably is an exoglycosidase. The exoglycosidase may be, for example, a neuraminidase, a galactosidase, a fucosidase, or a mannosidase. The substrate is preferably 4-methylumbelliferyl-N-acetyl-α-D-neuraminic acid, 4-methylumbelliferyl-α-L-fucoside, or 4-methylumbelliferyl-α-D-galactoside.

The amount of the cleaved 4-Mu group is preferably determined by fluorescence spectroscopy. More preferably, the amount of the 4-Mu product is determined by performing fluorescence spectroscopy using an excitation wavelength of about 360 nm and an emission wavelength of about 460 nm.

The method of the present invention measures enzyme activity in a kinetic assay, using substrates containing a cleavable 4-Mu side group, at the pH optimum of the enzyme. The method also provides a means to detect alterations in enzyme activity that are independent of protein expression levels. In the case of exoglycosidases, the fluorescence of the 4-Mu product at the pH optimum of the enzyme is considerably lower than it would be at the higher pH commonly used for measuring the fluorescence of the 4-Mu product. However, it is still sufficient to enable continuous assay of exoglycosidase activities at levels of the enzyme normally found in samples. Furthermore, the present method can be extended beyond the assays of exoglycosidases. The activities of other enzymes, such as endoglycosidases and heteropolysaccharide side chain-cleaving enzymes, may also be assayed by the present method, as long as the enzyme can cleave a 4-Mu group from a substrate bearing a cleavable 4-Mu side group. Examples of such substrates include, without limitation, 4-methylumbelliferyl-N-acetyl-α-D-neuraminic acid, 4-methylumbelliferyl-α-L-fucoside, 4-methylumbelliferyl-α-D-galactoside, 4-methylumbelliferyl-N-acetyl-α-D-glucosaminide, 4-methylumbelliferyl-α-L-arabinofuranoside, 4-methylumbelliferyl-α-L-arabinopyranoside, 4-methylumbelliferyl-β-D-cellotrioside, 4-methylumbelliferyl-β-D-galactoside, 4-methylumbelliferyl-α-D-glucoside, 4-methylumbelliferyl-β-D-glucoside, 4-methylumbelliferyl-β-D-glucuronide, 4-methylumbelliferyl-β-D-lactoside, 4-methylumbelliferyl-β-D-mannoside, and other substrates bearing a 4-Mu group and known to those in the art as appropriate substrates for the enzyme activity of interest.

From the results of these assays, enzyme kinetic parameters, such as initial velocity (Vi), Km, $K_{cat}$, and Vmax, can be determined through the use of standard plots and calculations well known to those in the art, such as the Lineweaver-Burk plot, the Hanes plot, or the Eadie-Hofstee plot. This information derived from these plots may be used to determine the true specific activity of the enzyme, regardless of the copy number of the enzyme inside the cell. For example, Km is an example of a kinetic parameter that is known to be independent of the enzyme concentration inside a sample. Furthermore, by using currently available robotic high throughput assay systems, a very high number of samples can be simultaneously assayed. The data so generated can thereafter be analyzed by automated data analysis methods known to those in the art. Thus, these kinetic assays, in combination with such high throughput enzyme assay systems, can be used to inexpensively assay the specific activities of multiple samples bearing mutant enzyme activities to determine the kinetic characteristics of the enzyme in each sample, without the need to purify the enzyme or determine the amount of enzyme expressed.

Similarly, the effects of various inhibitors of exoglycosidases may be studied more conveniently by using the kinetic assay of the present invention. Furthermore, substrate specificities of the enzymes may also be studied, and the characteristics of the enzymes with respect to these substrates can be determined. Thus, it is evident that the method of the present invention provides a powerful new tool for the study of these enzymes.

Although the present method is described below in the Experimental Details as using the yeast *Pichia pastoris*, it should also be evident that enzyme expression in other systems could be assayed. These include, without limitation, various prokaryotic systems (such as *E. coli*), eukaryotic systems, including other yeast systems (such as *Saccharomyces cerevisiae, Hansenula polymorpha, Yarrowia lipolytica, Schizosaccharomyces pombe, Kluyveromyces lactis* and *Schwanniomyces occidentalis*) insect systems (such as baculovirus-based systems), mammalian systems (such as CHO cells), and semi-synthetic or wholly synthetic expression systems (such as reticulocyte lysates). Expression of heterologous proteins in these systems are well known to those in the art.

Experimental Details

4-Methylumbelliferyl-N-acetyl-α-D-neuraminic acid sodium salt dehydrate (4-Mu-α-NeuAc) was purchased from Fluka Inc. 4-Methylumbelliferone, 4-methylumbelliferyl-α-L-fucoside (4-Mu-α-Fuc), and 4-Methylumbelliferyl-α-D-galactoside (4-Mu-α-Gal) were purchased from Sigma Chemical Co. (St. Louis, Mo). Coffee α-galactosidase was expressed and purified in the inventor's laboratory, and chicken liver α-fucosidase was purified in the inventor's laboratory. *Vibrio cholerae* neuraminidase was purchased from Sigma Chemical Co. BCA protein assay reagents were purchased from Pierce Chemical Co.

pH profile of 4-Mu: To characterize the pH-dependent fluorescence intensity of 4-Mu, 30 μL of a 4-Mu solution (1 nM and 10 nM in dH$_2$O) was added to 120 μL phosphate-buffered saline (PBS) at a final pH between 3.0 and 10.0. The fluorescence intensity was measured in a Bio-Tek FL500 fluorescence microplate reader at sensitivity 32, with excitation at 360±40 nm and emission at 460±40 nm. All fluorescence measurements were performed at these microplate reader settings.

Continuous exoglycosidase assay: Substrate stock solutions were diluted with PBS containing 1 mg/mL BSA. For neuraminidase, the pH of the substrate stock solution was 5.0; for α-galactosidase, the pH was 6.5; and for α-fucosidase, the pH was 7.0. These pH values are known in the art to be optimal for the corresponding enzyme activities. Substrate (50 μL) was first pipetted to each well in a microplate. To the sample wells, 100 μL of enzyme (3.36 mU neuraminidase; 0.16 mU α-fucosidase, or 1.04 mU α-galactosidase) was added. In the control wells, 100 μL of buffer replaced enzyme. Each sample was run in triplicate. After addition of enzyme, the wells were scanned every 30 seconds or 1 minute for up to seven minutes, at the settings indicated above. As a standard, 4-Mu in each buffer was also scanned.

The amount of 4-Mu produced in each reaction was calculated based on the fluorescence values obtained from the standards. Initial velocity (Vi) was derived from the slope of a linear regression analysis of the amount of 4-Mu produced over time. Km (mM) and Vmax (U/mg) were calculated from a Lineweaver-Burk plot. Where the concentration of enzyme was unknown, as in the *P. pastoris* culture supernatant, V'max (U/mL) was calculated, where mL was the volume of the supernatant added to the assay.

Results

The fluorescence intensity of 4-Mu is pH-dependent. Referring now to FIG. 1, the fluorescence of 4-Mu (measured at both 1 nM and 10 nM) is greatest when the pH is above 9. As the pH decreases, the fluorescence intensity drops dramatically. The fluorescence intensity of 4-Mu at pH 6 is approximately one-tenth that at pH 10. Since a majority of exoglycosidases are most active below neutral pH, exoglycosidase activity is conventionally measured in the presence of a 4-Mu-linked substrate at the pH that is optimal for the enzyme activity, then a high pH buffer is added at the end of the assay to enhance the fluorescence intensity of the 4-Mu product. The fluorescence intensity due to the liberated 4-Mu is then measured, and the amount of 4-Mu produced is determined by comparison to a standard curve of 4-Mu concentration vs. fluorescence intensity.

Neuraminidase isolated from *Vibrio cholerae* exhibits maximal activity at a pH of 5.0. Therefore, to assay the *Vibrio cholerae* neuraminidase activity, the enzyme was incubated at a pH of 5.0 with 4-Mu-α-NeuAc, at concentrations from 0.033 mM to 1.0 mM. The fluorescence due to 4-Mu was recorded at one-minute intervals. The amount of 4-Mu produced was directly proportional to the incubation time, and remained so over the assay period. The initial velocity (Vi) was calculated by linear regression analysis of the data, and a Lineweaver-Burk plot constructed. The value obtained for the Km of neuraminidase was 0.307 mM, and for Vmax was 7.36 U/mg.

In the same manner, the reaction of α-galactosidase with 4-Mu-α-Gal and of α-fucosidase with 4-Mu-α-Fuc were measured in solutions at the optimal pH of 6.5 and 7.0, respectively. Values of Km=0.12 mM and Vmax=44.0 U/mg were obtained for α-galactosidase, and Km=0.017 and Vmax=5.89 U/mg were obtained for α-fucosidase. These values were in agreement with those obtained for each enzyme by a conventional endpoint assay. Therefore, it is feasible to measure exoglycosidase activity using 4-Mu-linked substrates in a pH range far lower than that conventionally employed for such substrates.

The utility of this kinetic assay system to screen yeast transformants expressing wild-type α-galactosidase was tested. Ten *Pichia pastoris* clones transformed with wild-type α-galactosidase cDNA were induced for enzyme expression. After induction, 1 μL of each culture supernatant was assayed, using 4-Mu-α-Gal as the substrate at four different subsaturating concentrations. Each substrate concentration was assayed in triplicate in each transformant. Since all the colonies were transformed with the same cDNA, the enzymes expressed should be structurally and kinetically identical. However, different copy numbers of the enzyme gene are often integrated into the *P. pastoris* chromosome during homologous transformation, and should lead to different levels of expression of the gene. The result should be differences in the values for enzyme activity for each clone, but substantially identical values for the Km, since this parameter is independent of the concentration of the enzyme withing the cell.

Referring now to Table 1, the values for Km for each transformant were very similar. This is reflected in the fact that the value obtained for the standard deviation (0.013) was only 7.8% of the mean value for Km (0.165). However, the enzyme activities (expressed as U/mL) measured at subsaturating levels of substrate varied greatly among transformants, ranging from a low of 0.091 to a high of 0.351, as shown in Table 1. In this case, the value for the standard deviation (0.086) was 42% of the mean value for the activity (0.204). This was as expected, because as noted above, the clones were all transformed with the identical gene, but each clone could be expected to integrate different copy numbers of the gene into the DNA of the cell.

Vmax (U/mg), like enzyme activity, depends on the amount of enzyme, and thus would be expected to vary widely among the isolates. Since the amount of enzyme in each sample was unknown, V'max (U/mL) was used in place of Vmax, where mL refers to the volume of the tested samples. Although the V'max values varied widely among isolates (standard deviation was 45% of the mean of V'max), as expected, the V'max/Activity values are similar (standard deviation was 6.1% of the mean of V'max/Activity (Table 1). Although the units appear identical (U/mL), the values for activity represent values measured in the experiments, while the V'max values are calculated from the data obtained in the experiments. The similarity among the values for the V'max/Activity ratios further indicates that the enzymes expressed in the different clones do not differ significantly in their specific activities. Conversely, differences in this ratio from the controls provide evidence that the clones contain mutated forms of the enzyme. Therefore, this assay provides a powerful method for screening mutated enzymes having novel properties associated with noticeable changes in enzyme kinetic parameters.

TABLE 1

| Sample | Activity (U/mL) | Km (mM) | V'max (U/mL) | V'max/Activity |
|---|---|---|---|---|
| 1 | .351 | .182 | .996 | 2.838 |
| 2 | .238 | .179 | .673 | 2.828 |
| 3 | .310 | .152 | .750 | 2.419 |
| 4 | .239 | .173 | .637 | 2.665 |
| 5 | .230 | .156 | .561 | 2.439 |
| 6 | .109 | .145 | .276 | 2.532 |
| 7 | .192 | .153 | .466 | 2.427 |
| 8 | .162 | .166 | .434 | 2.679 |
| 9 | .091 | .178 | .242 | 2.659 |
| 10 | .120 | .164 | .299 | 2.492 |
| Mean | .204 | .165 | .533 | 2.598 |
| Std. Deviation | .086 | .013 | .239 | 0.159 |

All patents and references mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for detecting the presence of an enzyme in a solution, comprising the steps of:
    contacting said solution with a substrate having a 4-methylumbelliferyl group at a pH optimal for the specific activity of said enzyme under conditions allowing cleavage of said 4-methylumbelliferyl group from said substrate by said enzyme; and
    determining the presence of said cleaved 4-methylumbelliferyl group in said solution without adjusting the pH of said solution.

2. The method according to claim 1, wherein said enzyme is a member selected from the group consisting of an exoglycosidase, an endoglycosidase and a heteropolysaccharide side chain-cleaving enzyme.

3. The method according to claim 2, wherein said enzyme is an exoglycosidase.

4. The method according to claim 3, wherein said exoglycosidase is one of neuraminidase, α-galactosidase, α-fucosidase, and α-N-acetylgalactosaminidase.

5. The method according to claim 1, wherein said substrate is one of 4-methylumbelliferyl-N-acetyl-α-D-neuraminic acid, 4-methylumbelliferyl-α-L-fucoside, and 4-methylumbelliferyl-α-D-galactoside.

6. The method according to claim 1, wherein said enzyme is an exoglycosidase and said substrate is one of 4-methylumbelliferyl-N-acetyl-α-D-neuraminic acid, 4-methylumbelliferyl-α-L-fucoside, and 4-methylumbelliferyl-α-D-galactoside.

7. The method according to claim 1, wherein said presence of said cleaved 4-methylumbelliferyl group is determined by fluorescence spectroscopy.

8. The method according to claim 7, wherein said fluoresence spectroscopy is performed using an excitation wavelength of about 360 nm and an emission wavelength of about 460 nm.

9. A method for measuring a kinetic parameter of an enzyme in a solution, comprising the steps of:
    contacting said solution with a substrate having a 4-methylumbelliferyl group at a pH optimal for the specific activity of said enzyme under conditions allowing cleavage of said 4-methylumbelliferyl group from said substrate by said enzyme; and determining a value for said kinetic parameter of said enzyme from the amount of said cleaved 4-methylumbelliferyl group generated in said solution without adjusting the pH of said solution.

10. The method according to claim 9, wherein said enzyme is a member selected from the group consisting of an exoglycosidase, an endoglycosidase and a heteropolysaccharide side chain-cleaving enzyme.

11. The method according to claim 9, wherein said enzyme is an exoglycosidase.

12. The method according to claim 11, wherein said exoglycosidase is one of neuraminidase, $\alpha$-galactosidase, $\alpha$-fucosidase, and $\alpha$-N-$\alpha$-acetylgalactosaminidase.

13. The method according to claim 9, wherein said substrate is one of 4-methylumbelliferyl-N-acetyl-$\alpha$-D-neuraminic acid, 4-methylumbelliferyl-$\alpha$-L-fucoside, and 4-methylumbelliferyl-$\alpha$-D-galactoside.

14. The method according to claim 9, wherein said enzyme is an exoglycosidase and said substrate is one of 4-methylumbelliferyl-N-acetyl-$\alpha$-D-neuraminic acid, 4-methylumbelliferyl-$\alpha$-L-fucoside, and 4-methylumbelliferyl-$\alpha$-D-galactoside.

15. The method according to claim 9, wherein said presence of said cleaved 4-methylumbelliferyl group is determined by fluorescence spectroscopy.

16. The method according to claim 15, wherein said fluorescence spectroscopy is performed using an excitation wavelength of about 360 nm and an emission wavelength of about 460 nm.

17. The method according to claim 9, wherein said enzyme activity is expressed as a member selected from the group consisting of units of cleaved 4-methylumbelliferyl group per unit of time and units of cleaved 4-methylumbelliferyl group per unit of time per unit of enzyme.

* * * * *